US006761913B2

(12) United States Patent
Butters et al.

(10) Patent No.: US 6,761,913 B2
(45) Date of Patent: Jul. 13, 2004

(54) EXTRACTS OF CELERY SEED FOR THE PREVENTION AND TREATMENT OF PAIN, INFLAMMATION AND GASTROINTESTINAL IRRITATION

(75) Inventors: Desley Ethel Butters, Stones Corner (AU); Craig Kendall Charles Davis, Chapel Hill (AU); Ross Peter McGeary, St Lucia (AU); Michael Christopher Powanda, Mill Valley, CA (US); Kim Drummond Rainsford, Baslo (GB); Michael Wellesley Whitehouse, Stones Corner (AU)

(73) Assignee: International Celery Development Alliance PTY. Ltd., Queensland (AU)

( * ) Notice: Subject to any disclaimer, the term of this patent is extended or adjusted under 35 U.S.C. 154(b) by 0 days.

(21) Appl. No.: 10/421,202

(22) Filed: Apr. 22, 2003

(65) Prior Publication Data

US 2003/0206980 A1 Nov. 6, 2003

Related U.S. Application Data

(63) Continuation-in-part of application No. 10/032,956, filed on Oct. 26, 2001, now Pat. No. 6,576,274, which is a continuation of application No. 09/432,140, filed on Nov. 2, 1999, now Pat. No. 6,352,728.

(30) Foreign Application Priority Data

Nov. 4, 1998 (AU) ............................................. PP6891
Dec. 30, 1998 (AU) ............................................. PP7975

(51) Int. Cl.$^7$ .............................................. A61K 35/78
(52) U.S. Cl. ...................... 424/758; 424/776; 424/725; 514/159; 514/165
(58) Field of Search ................................ 424/758, 776, 424/725; 514/159, 165

(56) References Cited

U.S. PATENT DOCUMENTS

| 3,935,310 A | 1/1976 | Homan |
| 4,824,570 A | 4/1989 | Bethuel et al. |
| 5,252,729 A | 10/1993 | De Crosta et al. |

FOREIGN PATENT DOCUMENTS

| IN | 445/M94 | 5/1994 |
| WO | WO 95/00157 | 1/1995 |

OTHER PUBLICATIONS

Cu, et al., "Extraction of Volatile Compounds of Lavage Root, Celery Seed and Carrot Seed by Different Solvents," Aspect publishing, London, (1990) pp. 89–97.
Hirschhorn, H.H., The Home Herbal Doctor, Parker Publishing Co., Inc., West Nyack, New York, 1982, p. 43.
Kapoor, (1990) CRC Handbook of Ayurvedic Medicinal Plants CRC Press, Inc., Boca Raton p. 44.
Lam et al., J. Argic. Food Chem., vol. 39, pp. 680–682, 1991.
Lewis, et al., (1985) "The Anti–Inflammatory Activity of Celery Apium graveolens L. (Fa. Umbelliferee)," Int. J. Crude Drug Res. vol. 23(1):27–32.
Atta et al., "Anti–nociceptive and anti–inflammatory effects of some Jordanian medicinal plant extracts." Journal of Ethnopharmacology, vol. 60, No. 2, Mar. 1998, p. 117–124, XP002194236, ISSN: 0378–8741 (Relevant to claim: 8–10, 12, 14–18).
Database WPI, Section Ch, Week 199424, Derwent Publications Ltd., London, GB; Class D23, AN 1994–197407, X002194237 & JP 06 136384 A (Shoukuhin Sangyo High Separation System), May 17, 1994 *abstract* (Relevant to claim: 1–7, 11).
Patent Abstracts of Japan, vol. 13, No. 419 (C–637), Sep. 18, 1989 & JP 01 157915 A (Lion Corp), Jun. 21, 1989, *abstract* (Relevant to claim 1, 8–10, 12–18).
Moyler, D.A., "Extraction of Essential Oils with Carbon Dioxide," Flavour and Fragrance Journal (1993) vol. 8(5):pp.:235–247.
Whitehouse, et al. (1997) "Anti–Inflammatory Activity of a Lipid Fraction (Lyprinol) from the NZ Green–Lipped Mussel," Inflammopharmacology vol. 6:237–246.
Zheng et al. Nutrition and Cancer, vol. 19, No. 1, pp. 77–86, 1993.

*Primary Examiner*—Francisco Prats
*Assistant Examiner*—Susan D. Coe
(74) *Attorney, Agent, or Firm*—James S. Keddie; Bozicevic, Field, & Francis LLP

(57) ABSTRACT

Biologically active extracts of celery seed are produced by controlled ethanolic extraction, distillation and drying, and further processing by supercritical fluid extractions (SFE), and may be further fractionated by column fractionation, distillation, LiAlH reduction and the like. These extracts possess activity for the treatment and prevention of acute and chronic pain, inflammation and gastrointestinal irritation.

8 Claims, No Drawings

EXTRACTS OF CELERY SEED FOR THE PREVENTION AND TREATMENT OF PAIN, INFLAMMATION AND GASTROINTESTINAL IRRITATION

CROSS REFERENCE TO RELATED APPLICATIONS

This application is a Divisional of prior U.S. application Ser. No. 10/032,956 filed Oct. 26, 2001, now U.S. Pat. No. 6,576,274 which application is a Continuation of prior U.S. application Ser. No. 09/432,140 filed Nov. 2, 1999, now U.S. Pat. No. 6,352,728 which claims the benefit under 35 U.S.C. § 119(a) of prior foreign Australian application nos. PP7975 filed Dec. 30, 1998 and PP6891 filed Nov. 4, 1998, all of which are incorporated herein by reference.

FIELD OF THE INVENTION

This invention relates to the preparation and use of biologically active celery seed extracts that alone and in combination with drugs and herbal medicines can be used to prevent and treat pain, inflammation and gastrointestinal irritation.

BACKGROUND OF THE INVENTION

The prevention or inhibition of inflammation and pain is of significant concern, particularly for those afflicted with arthritis and other musculoskeletal ailments, including sports-related injuries. Pain usually accompanies inflammation and vice versa.

Acute and chronic pain and inflammation are often treated with anti-inflammatory/analgesic compounds such as aspirin, ibuprofen and naproxen (K. D. Rainsford (1996) New Developments in Anti-Rheumatic Therapy. CRC Press Inc, Boca Raton). There are, however, appreciable risks from these drugs in particular gastro-intestinal ulceration and bleeding (Rainsford ibid). While another commonly-used pain-killing drug, acetaminophen does not have this side-effect, its benefits and range of uses is limited because it does not have anti-inflammatory activity. Acetaminophen is less effective in control of pain because it does not control the inflammatory reactions that often accompany pain, especially that from chronic conditions such as arthritis (Rainsford ibid). Furthermore, there is considerable concern about use of acetaminophen, especially at over-the-counter doses, because of the risks of severe and, rarely, irreversible liver damage that can lead to death (K. D. Rainsford and M. C. Powanda (1998) Safety and Efficacy of Non-prescription (OTC) Analgesics and NSAIDS, Kluwer Academic Publishers, Dordrecht; R. P. Rapp et al (1997) The Pill Book Guide to Over-the-Counter Medications. Bantam Books, New York).

Prostaglandins are a family of compounds that have been identified as playing a significant role in inflammation. Prostaglandins are produced throughout the body and are derived from enzymatic action on a common substrate, arachidonic acid. The first step in prostaglandin synthesis is the oxygenation of arachidonic acid by the enzyme cyclooxygenase. The oxygenated prostaglandin precursors are subject to further enzymatic processes which provide the various members of the prostaglandin family.

Recently, new anti-inflammatory/analgesic drugs have been developed that have been claimed to have lower propensity to cause gastro-intestinal ulcers and bleeding. These drugs have been designed to specifically inhibit the activity of cyclo-oxygenase-2 (COX-2). They do not, in contrast, affect the production of those prostaglandins that are derived from another enzyme, cyclo-oxgenase-1 (COX-1), which are important for protection of the gastro-intestinal tract against injury either from irritating substances or bacteria.

COX-1 is inhibited by aspirin and other older anti-inflammatory/analgesic drugs and this is a major factor underlying their ulcer-producing activity (Rainsford ibid). Some recent evidence suggests, however, that these new COX-2—selective drugs may not be without some gastro-intestinal irritancy, and may even have other adverse effects in the kidney in a similar manner to that from the older anti-inflammatory/analgesics. It is clear that there is a need for drugs that have anti-inflammatory and analgesic activity comparable with that of aspirin and related drugs but without the gastrointestinal ulcerogenic effects and bleeding that occurs with these drugs.

Relevant Literature

Wild celery is noted in the Ayurvedic pharmacopoeia for treatment for headaches and as a diuretic and spasmolytic (CRC Handbook of Ayurvedic Medicinal Plants, 1990, p 44, CRC Press Inc., Boca Raton). It is included in the 1983 British Herbal Pharmacopoeia as a treatment for arthritis and gout. The seed oil is used in perfumery, for flavoring food products and liqueurs, and also as a cercaricide. According to the Physician's Desk Reference for Herbal Medicines (1998, Medical Economics Company Inc, Montvale N.J.), "Preparations of celery are used as a diuretic, for blood purification, for regulating elimination of the bowels, for glandular stimulation, rheumatic complaints, gout, gall and kidney stones. Celery is also used for weight loss due to malnutrition, for loss of appetite, exhaustion and as a prophylactic for nervous unrest. The efficacy for the claimed applications is not documented."

Lewis et al. (Int. J. Crude Drug Res., 1985;23:27–32) claimed anti-inflammatory compounds were present in aqueous extracts of the stem of cultivated celery. They could not identify the major active compounds, merely describing them as "unidentified polar substance(s)".

Preclinical assessment of over the counter medications, including herbal medicines, available in Australia for the treatment of arthritis and rheumatism demonstrated that some, but clearly not all, celery seed extracts, have the capacity to treat and prevent inflammation (Whitehouse M W et al. Inflammopharmacology, 1999:7:89–105).

An International Patent Application, WO 95/00157 (Applicant: MOBIUS CONSULTANCY PTY. LTD.; Inventor: B. Daunter) makes claims for relief of inflammatory complaints based on plant extracts of the genus Umbelliferae, especially celery, parsley and dill, particularly citing alcohol-soluble purported constituents of the celery seed oil, namely phthalides, isobenzofurans, naphthoquinones, and some derivatives, e.g., isoindolones.

Indian process patent A.P.R. No. 445/M/94 was issued in 1994 to Life Care Products Limited for a method of preparing pharmacologically active extracts from celery seed.

SUMMARY OF THE INVENTION

Compositions and methods are provided for the prevention and treatment of pain, inflammation and gastrointestinal irritation. The compositions comprise a purified, biologically active extract of celery seed, and may further be co-formulated with an additional analgesic or anti-inflammatory compound, e.g. non-steroidal anti-inflammatory drugs (NSAID), herbal medicines, etc. The compositions may be formulated for use in oral or topical preparations. Preparations of interest include pharmaceutical preparations, foods, lotions, and the like.

In a preferred embodiment, the biologically active extract of celery seed is prepared by supercritical fluid extraction. An alcoholic extract of fresh celery seed is mixed with a suitable adsorbant, and then subjected to supercritical fluid extraction. Optionally, the resulting product is further treated or fractionated. This product may be prepared in a pharmaceutical formulation for treatment of inflammation, pain, and/or gastrointestinal irritation.

In one embodiment of the invention, a biologically active formulation of celery seed extract is administered to provide a gastroprotective effect, or for the healing of gastrointestinal ulcers. In another embodiment of the invention, a combined formulation with an NSAID reduces or prevents gastrointestinal irritation associated with the NSAID activity. Such a combined formulation with an NSAID may also provide for a synergistic treatment of inflammation and pain.

DETAILED DESCRIPTION OF THE PREFERRED EMBODIMENTS

Purified extracts of celery seed are provided for use in pharmaceuticals to treat pain, inflammation and gastrointestinal irritation. These extracts may also be co-formulated with other analgesic or anti-inflammatory compounds, e.g. non-steroidal anti-inflammatory drugs (NSAID), herbal, medicines, etc. In particular, the purified extracts are used in methods to relieve acute, as well as chronic pain and inflammation, and to provide gastroprotection, e.g. against drug-induced gastrotoxicity, ulcer healing, etc.

A preferred celery seed extract is produced by supercritical fluid extraction of the starting product. This supercritical fluid extract is characterized by a 5–10 fold increase in specific activity when tested in an experimental model of polyarthritis which was induced in rats by injecting a mycobacterial arthritogenic adjuvant, Whitehouse et al. (1997) Inflammopharmacology 5:237–246. This supercritical fluid extract also includes more highly purified fractions derived therefrom. In addition to the biological activities described above, the supercritical extract can be used at doses comparable to existing NSAIDs to provide relief from acute pain in as little as a single dose.

This invention includes biologically active celery seed extracts having anti-inflammatory activity wherein a dose of 80 mg/kg, preferably of 50 mg/kg, also preferably of 30 mg/kg, also preferably of 20 mg/kg, also preferably of 10 mg/kg, also preferably of 5 mg/kg, of the extract exhibits the same or greater anti-inflammatory activity as 300 mg/kg of aspirin in the anti-inflammatory animal model disclosed in Whitehouse et al., (1997) *Inflammopharmocology* 5:237–246 (hereinafter "the Whitehouse anti-inflammatory animal model").

This invention includes biologically active celery seed extracts having analgesic activity wherein a dose of 80 mg/kg, preferably of 50 mg/kg, also preferably of 30 mg/kg, also preferably 20 mg/kg, also preferably of 10 mg/kg, also preferably of 5 mg/kg, of the extract exhibits the same or greater analgesic activity as 50 mg/kg, preferably as 100 mg/kg, also preferably as 200 mg/kg, of ibuprofen in the analgesic animal model disclose in Randall and Sellito (1957) *Arch. Int. Pharmacodyn. Ther.* 111: 409–419 (hereinafter "the Randall and Sellito analgesic animal model).

This invention includes biologically active celery seed extracts having gastroprotective activity wherein a dose of 80 mg/kg, preferably of 50 mg/kg, also preferably of 30 mg/kg, also preferably of 20 mg/kg, also preferably of 10 mg/kg, also preferably of 5 mg/kg, of the extract reduces by at least about 50%, preferably by at least 70%, the number of gastric lesions elicited by a probing dose of ibuprofen in the gastroprotection animal model disclosed in Rainsford and Whitehouse (1992). *J Pharm. Pharmacol.* 44:476–482 (hereinafter "the Rainsford and Whitehouse gastroprotection animal model.

This invention also includes biologically active celery seed extracts having combinations of both the anti-inflammatory and/or pain activity and the gastroprotective activity disclosed in the previous three paragraphs.

Before the present invention is described, it is to be understood that this invention is not limited to the particular embodiments described, as such methods, devices, and formulations may, of course, vary. It is also to be understood that the terminology used herein is for the purpose of describing particular embodiments only, and is not intended to limit the scope of the present invention which will be limited only by the appended claims.

It must be noted that as used herein and in the appended-claims, the singular forms "a," "an," and "the" include plural referents unless the context clearly dictates otherwise, and includes reference to equivalent steps and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

Biologically active celery seed extract: as used herein, the term biologically active celery seed extract (CSE) generically refers to a natural product derived from celery seed, or a pharmaceutically active equivalent thereof, which is active in suppressing inflammation, reducing pain, and/or protecting from gastrointestinal irritation. Where specific extracts or fractions thereof are intended, they may be referred to specifically, for example an alcoholic extract (A-CSE), supercritical fluid extract (S-CSE), etc., as will be described below. The biological activity may be determined by the use of various assays, as known in the art. For some purposes, e.g. in the treatment of gastrointestinal irritation, an alcohol extract of fresh celery seed (A-CSE) may be used. Generally, however, such an alcoholic extract is further refined by supercritical fluid extraction (S-CSE), and may then be additionally treated, as described herein.

Assays for determination of biological activity include animal models for pain, inflammation, and gastroprotection. For example, a suitable animal model for evaluating anti-inflammatory activity is described by Whitehouse et al. (1999) Inflammopharmacology 7:89–105. In an exemplary assay, polyarthritis was initiated by injecting 800 µg of heat-killed Mycobacterium tuberculosis suspended in squalene into the tail vein of rats. Activity of disease was assessed by measuring the swelling of all four paws with a micrometer screw gauge. An overall arthritis score was independently assessed. In order to be considered biologically active as an anti-inflammatory agent, the extract will usually have an activity greater than or equal to 300 mg/kg of aspirin in such an assay. For A-CSE, significant biological activity has been shown at about 100–350 mg/kg. For S-CSE significant biological activity comparable to NSAIDs such as ibuprofen, are seen at a dose of less than about 50 mg/kg, and may-be seen at a dose of less than about 10 mg/kg in this assay.

An exemplary assay for pain is described by Randall L O and Selilito J J, Arch Int Pharmacodyn Ther. 1957:111:409–419.

Suitable assays for gastroprotection include, inter alia, those described by Rainsford and Whitehouse (1992) *J. Pharm. Pharmacol.* 44:476–482. This model comprises oral or parenteral non-steroidal anti-inflammatory drugs (NSAIDs) given to rats whose gastrointestinal mucosa is pre-sensitized by prior development of arthritis or oleyl alcohol-induced inflammation. The animals are pre-sensitized by injection of an arthritogenic adjuvant or 0.1 ml oleyl alcohol 5 days prior to the assay. The animals are then fasted for 16 hours and given a standard dose of 50 mg/kg ibuprofen free acid or Nurofen®. A biologically active celery seed extract will reduce the number of haemorrhagic lesions in such an animal model by at least about 50%, usually by at least about 70%. Co-administration of the celery extract in doses of not more than about 150 mg/kg of A-CSE or not more than about 20 mg/kg of S-CSE, administered in a volume of 10 ml/kg, consistently reduced by 70 percent the mean number of gastric lesions elicited by the Ibuprofen at this probing dose (50 mg/kg).

Alcoholic celery seed extract (A-CSE): is a commercially available concentrated extract of fresh (green) celery seed, such as that supplied by Beagle International Pty. Ltd., Nerang, Qld. Australia, as a pungent green paste (GP). Methods for the production of such a green paste are described in Indian process patent A.P.R. No. 445/M/94, issued May 27, 1994.

Briefly, celery is purposely grown in the Punjab Northern India for its seed. Harvesting and winnowing is carried out mechanically. The seeds are plate ground, for bruising, cracking, or fracturing, but with care not to destroy the seed. Extraction takes place in a stainless steel "kettle" extractor, or any other lined vessel for a minimum of 72 hours. Alcohols such as isopropylalcohol, ethanol or methanol, grade IP/BP/USP are used, commonly in a ratio of 1 part seed to not less than 3 parts nor more than 10 parts alcohol by weight of plant material to solvent. During the extraction time agitation of the mixture is preferred.

The solvent rich material is removed from vessels and distillation is carried out under vacuum at a temperature between 30 and 60° C. in a vacuum between 300 to 750 mm mercury, to produce the crude extract. This extract is dried at 30 to 35° C. and at a pressure of 650 to 750 mm of mercury which conditions will normally give the optimum dryness. This drying process generally takes between 10 and 24 hours.

Supercritical Fluid Extraction. The alcoholic celery seed extract described above may be further purified by supercritical fluid extraction, to yield a product termed S-CSE (supercritical fluid celery seed extract), which term also includes fractions derived therefrom, as described below. Supercritical fluid extraction methods are known in the art. Generally, above a critical temperature ($T_c$) and pressure ($P_c$) a vapor and a liquid of the same substance have the same density. In this state the fluid cannot be liquified by further increasing the pressure. A supercritical fluid state results when the substance is maintained at its $T_c$ and $P_c$ whereby a transition from gas/liquid to supercritical liquid occurs. For example, a description of the phase changes in the gas ($CO_2$) and the conditions at which the gas becomes a supercritical fluid (SCF) are described in U.S. Pat. No. 4,749,522. The supercritical fluid extraction of plant materials is described in U.S. Pat. No. 5,252,729.

An apparatus for supercritical extraction is made up of an extraction cell that is housed in a chamber for controlling temperatures and exit pressures. The supercritical fluid (i.e. extracting mobile phase) is pumped into the extraction cell through a pressure regulating restrictor and into a vessel which serves as a trap. Pressure is maintained by back pressure regulators. As the supercritical fluid passes through the plant material containing the desired compound, the supercritical fluid removes the compound from the plant material. As the supercritical fluid containing the desired compound leaves the chamber, fluid transforms into gas, which passes through or is injected (i.e. bubbled) into a trapping vessel. The desired compounds extracted from the plant material are concentrated in the trapping vessel.

Representative extracting (solvating) mobile phase components of interest in the present invention include the elemental gases such as helium, argon, nitrogen and the like; inorganic compounds such as ammonia, carbon dioxide, water and the like; organic compounds such as C-1 to C-5 alkanes or alkyl halides such as monofluoro methane, butane, propane, carbon tetrachloride, and the like; or combinations of any of the above. A supercritical fluid can be modified by the addition of inorganic and/or organic compounds as listed above, called modifiers. By determining the known properties of the desired compound as well as the gas specifications, including supercritical temperatures and pressures, one of ordinary skill in the art can select those components or any combinations thereof suitable for the extraction process.

The plant material is contacted with the supercritical fluid at temperatures ranging from about 30° C. to about 300° C., preferably from about 30 to 40° C. The pressure employed should be sufficient to maintain the supercritical fluid, and can be increased from ambient atmosphere pressure to about 400 atmospheres or more, preferably between about 100 and 300 atmospheres. Preferably, the apparatus is programmed to maintain slow incremental increases in pressure to achieve extraction of the compound from the plant material.

In a preferred embodiment, the A-CSE which may be admixed with an adsorbent, e.g. a diatomaceous earth, for further processing by supercritical fluid extractions (SFE). Usually the supercritical fluid used to further purify the A-CSE is carbon dioxide which may be admixed with methanol. Typically, after using liquid carbon dioxide to extract sorbed A-CSE, a pungent amber liquid (S-CSE) is obtained representing approximately 15% (w/w) of the original A-CSE. Typically SFE results in a 5–10 fold increase in specific activity (Table 2) when starting with A-CSE.

Additional Processing. The S-CSE may be further processed to give various subfractions by distillation, hydrogenation, reduction with $LiAlH_4$, double reduction, hydrolysis, hydrolysis and oxidation, and column fractionation. This additional processing was used to determine that the gastroprotective activity could be separated from the anti-inflammatory activity in S-CSE. In addition, by measuring the markers that characterize these subfractions, it was possible to eliminate potential candidate molecules, such as the phthalides, from consideration as components of the anti-inflammatory activity. Because the fractions were assayed without further purification, the results are semi-quantitative, not readily allowing calculation of specific activity. However there appears to be a substantial increase in specific activity, e.g. column fraction 1 contains only 37 mg from the original 1000 mg applied to the column and has comparable activity, therefore an increase in specific activity by about an order of magnitude.

Fractions of interest from such processing steps include a column fraction obtained from chromatographing S-CSE on a silica column and collecting the eluate in the fraction in 1–20% diethyl ether in light petroleum (S-CSE fraction 1); or the fraction that elutes with 100% diethyl ether (S-CSE fraction 3). It is found that S-CSE fraction1 retains substantially all the anti-inflammatory activity of the S-CSE, but has lost a substantial amount of the gastroprotective activity.

Other fractions of interest include the distillation residues obtained from distillation at 150° C. and 1.0 mm Hg. Reduction by hydrogenation over a palladium catalyst or with LiAlH4 or both results in retention of substantially all of the anti-inflammatory activity, although a double reduced fraction shows no gastro-protective activity.

Assay Systems: An experimental polyarthritis was induced in rats by injecting a mycobacterial arthritogenic adjuvant, Whitehouse et al. (1997) Inflammopharmacology 5:237–246. A chronic (established) inflammation, polyarthritis was initiated in female Dark Agouti or Wistar rats on "Day O" by injecting 800 $\mu$g heat-killed Mycobacterium tuberculosis in 100 $\mu$l squalane (constituting a 'complete' Freund's adjuvant) into the tail base. The test drugs/formulations were given on and after Day 10 to treat the established arthritis. The polyarthritis is usually manifest from Day 12 as local inflammation and ulceration in the tail, inflammation in all paws and inflammatory lesions on forepaws and ears. Inflammation was evaluated using a micrometer to measure changes in rear paw and tail thickness, and by visual estimates of the severity of front paw swelling and inflammation. Animals were sacrificed by cervical dislocation on or before Day 18 and checked for gastric lesions and other non-articular pathologic changes. Statistical significance was evaluated by using the standard Student 't test' described in "Statistical Methods", 8th edition, G W Snedecor, W G Cochran, Iowa State University Press, Ames, Iowa (1989).

To evaluate gastric injury caused by aspirin/NSAIDs, administered alone or in combination with the celery extract, these drugs were given orally to rats which had been pre-sensitised by disease stress (K D Rainsford, M W Whitehouse. (1992) J.Pharm. Pharmacol. 44:476–482). The disease stress was induced five days previously either by injecting an arthritigenic adjuvant or 0.1 ml oleyl alcohol into the tail base to incite severe local inflammation. Rats were permitted free access to water but routinely fasted for 16 hours prior to dosing them for the gastro toxicity assay, to facilitate inspection of the gastric lining post mortem. The animals were sacrificed 2.5 hours after the oral administration of aspirin/NSAID. A-CSE or S-CSE was given orally within 20 seconds of the aspirin/NSAID. The number (N) and severity (S, graded on a score of 0 to 4 based on increasing area of injury) of gastric lesions as well as the percentage incidence of animals (%I) with gastric damage was recorded. The lesion index (LI) was then calculated as: LI=N/n+S/n+%I/10, where n=number of animals per group. Statistical significance was determined using the Mann-Whitney U-test as described in Snedecor and Cochran, Iowa State University Press, Ames, Iowa (1989).

The pain model used was that based on the standard model of Randell & Selitto in which rat paws were pre-swollen with a carageenan injection and then pressure sensitivity assessed with or without a dose of celery extract (Randall L O, Sellito J J Arch Int Pharmacodyn Ther 1957:111:409–419).

Animals were pre-sensitised either (i) with a tail base injection of a low level non-arthritigenic adjuvant (150 microgram M. tuberculosis/1.0. ml squalane per rat) 15 days previously (to confirm no arthritis) or (ii) injected 48 hours previously in each rear paw with an edema-inducing dose of carrageenan (0.6 mg/0.1 ml saline) and the paw swelling allowed to subside.

After either pretreatment, animals were rechallenged with a further paw injection of carrageenan (0.6 mg/foot) followed by oral dosing of test drugs. Pressure was applied to each rear paw 2 and 3.5 hours later with a spring-loaded forceps and the vocalisation threshhold recorded.

Anti-inflammatory drug. The present method may employ combination formulations of pharmaceuticals or nutraceuticals with anti-inflammatory drugs and herbal medicines. Herbal medicines of interest include, but not restricted to, active fractions from certain herbal preparations such as nettles (*Urtica dioica*) or turmeric (*Curcuma longa*); marine or terrestial animal products, e.g. bioactive lipids from *Perna canaliculus, Dromaius nova hollandiae*, etc. In addition, other known synergists, e.g. stable prostaglandin analogues such as misoprostol, etc., may potentiate the therapeutic effects of the celery extracts.

Such compositions may include any variety of those drugs generally classified as nonsteroidal anti-inflammatory drugs (NSAIDs). By way of example, these drugs include ibuprofen, piroxicam, salicylate, aspirin, naproxen, indomethacin, diclofenac, or any mixture thereof. Also of interest are NSAIDs such as ketoprofen, oxaprozin, etodolac, ketorolac and nabumetone.

By way of example and not limitation, NSAID's useful in the practice of the invention, include fenoprofen calcium, nalfon, flurbiprofen, Ansaid, ibuprofen, ketoprofen, naproxen, anaprox, aflaxen, oxaprozin, diclofenac sodium, diclofenac potassium, cataflam, etodolac, indomethacin, ketorolac tromethamine, nabumetone, sulindac, tolmetin sodium, fenamates, meclofenamate sodium, mefenamic acid, piroxicam, salicylic acid, diflunisal, aspirin, oxyphenbutazone, and phenylbutazone.

Combination formulations: The CSE compositions of the invention may also contain other therapeutically active agents. Of particular interest are combinations with other agents capable of additive or synergistic effect in achieving a therapeutic result, e.g. where a different or complementary pathway is affected by each of the active agents. Of particular interest is a formulation or administration in combination with a second anti-inflammatory drug, as described above. The combination of active agents provides for an additive, or a synergistic effect in treating inflammation and pain. Where the second anti-inflammatory drug causes gastric irritation, the CSE provides a gastro-protective effect, and reduces this undesirable side-effect.

Specifically, in one embodiment of the invention the CSE serves to enhance the desirable anti-inflammatory activity of NSAIDs, while reducing the undesirable gastric irritation the NSAIDs produce. In this way a dual benefit is obtained from the combination therapy. Such a formulation also provides a method of maintaining and/or enhancing the therapeutic activity of a non-steroidal anti-inflammatory drug in the presence of a drug that reduces or inhibits gastric secretion, e.g. omeprazole, which drug may include an H2 receptor blocker, e.g. Zantac, Tagamet, nizetidine, etc., or proton pump inhibitor, e.g. lansoprazole.

For the treatment of pain, the biologically active celery seed extracts of this invention are effective either alone or in combinations with one or more compounds from other broad classes of compounds that have analgesic activity, including, but not limited to: opioids, cannabinoids, steroids, non-narcotic analgesics (such as acetaminophen, non-steroidal anti-inflammatory analgesics, salicylates whether acetylated or not, and the newer classes of cyclooxygenase 2 inhibitors), leukotriene inhibitors, psychotropic drugs (such as antidepressants, anticonvulsants, neuroleptics and anti-anxiety agents), local anaesthetics, epidural analgesics (including, but not limited to, local anaesthetics, opioids, alpha 2 adrenergic agonists) and other analgesics that may act through channel modifiers (blockers or openers of potassium, calcium or sodium channels), ionotropic or metabotropic excitatory amino acid receptor classes (including, but not limited to, modifiers of the N-methyl-D-aspartic acid, alpha-amino-3-hydroxy-5-methyl-4-isooxazolepropionic acid, kainic acid or metabotropic receptor), inhibitory amino acids (including, but not limited to, modifiers of the gamma-amino butyric acid, glycine and adenosine receptors), second messenger systems (including, but not limited to, isoforms of protein kinase C, protein kinase A, phospholipase A2, nitric oxide synthase, phospholipase C, cyclic AMP, cyclic GMP, g-protein coupled), capsaicin, bradykinin, serotonin, adrenergic agents, peptide modifiers (that alter activity of peptides such as substance P, calcitonin gene related peptide, vasoactive intestinal polypeptide, neuropeptide Y), modifiers of immediate early genes (including, but not limited to, members of the fos, myc and jun family), modifiers of the immune system (including, but not limited to, interleukins).

The combined used of CSE and other agents has the advantages that the required dosages for the individual drugs may be lower, and the onset and duration of effect of the different drugs complementary. In the combined therapy, the different active agents can be delivered together or separately, and simultaneously or at different times within the day. Moreover the compounds may be administered by any convenient and effective route, e.g. orally, by injection, rectally or transdermally. Preferably, where the agents are orally active, administration will be oral and the different agents will be administered substantially simultaneously, preferably as a composition containing both agents.

Treatment of pain: For the treatment of pain, the biologically active celery seed extracts of this invention are effective in the prevention or treatment of one or more acute or chronic pain conditions including, but not limited to: peripheral nerve disorders (i.e. peripheral neuropathies) that may be from the broad class of mononeuropathies or polyneuropathies, pain following amputation, herpes zoster, pain due to anxiety, neuroses, depression and other psychic illnesses, arthritis and periarthritis disorders (including, but not limited to, osteoarthritis, rheumatoid arthritis, ankylosing spondylitis, gout, infectious arthritis), myofascial pain syndromes, pain due to musculoskeletal injuries and conditions (including, but not limited to, fractures, dislocations, sprains, strains, sports injuries, overuse injuries such as tendentious, traumatic muscle spasms), pain of bone origin including those of infectious and metabolic origin, pain arising from neoplasms and cancers, postoperative pain, post-burn pain, pain of dermatological origin (including, but not limited to, vasculitis, ulcers, painful infections and inflammations, necrosis), pain due to vascular disease (including, but not limited to, pain arising from peripheral artery disease, diseases of the microcirculation, peripheral veins, lymphatics and small artieries), pain of cranial nerve origin (including, but not limited to headache and the broad categories of migraine), pain arising from the orofacial regions (including, but not limited to, pain arising from the teeth, gingival and soft and hard palate), visceral pain arising from the chest and abdominal regions, pain from the pelvis, perineum and genitalia, and pain from the upper and lower extremities.

Pharmaceutical Formulation: The CSE may be combined with a pharmaceutically acceptable carrier, which term includes any and all solvents, dispersion media, coatings, anti-oxidant, isotonic and absorption delaying agents and the like. The use of such media and agents for pharmaceutically active substances is well known in the art. Except insofar as any conventional media or agent is incompatible with the active ingredient, its use in the therapeutic compositions and methods described herein is contemplated. Supplementary active ingredients can also be incorporated into the compositions.

The formulation may be prepared for use in various methods for administration. The formulation may be given orally, by inhalation, applied topically or may be injected, e.g. intravascular, intratumor, subcutaneous, intraperitoneal, intramuscular, etc.

The dosage of the therapeutic formulation will vary widely, depending upon the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc. to maintain an effective dosage level. In some cases, oral administration will require a higher dose than if administered intravenously.

The CSE of the invention can be incorporated into a variety of formulations for therapeutic administration. More particularly, the complexes can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the CSE can be achieved in various ways. The CSE may be systemic after administration or may be localized by the use of an implant that acts to retain the active dose at the site of implantation.

The following methods and excipients are merely exemplary and are in no way limiting. For oral preparations, the CSE can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The CSE can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The CSE can be utilized in aerosol formulation to be administered via inhalation. The compounds of the present invention can be formulated into pressurized acceptable propellants such as dichlorodifluoromethane, propane, nitrogen and the like.

Furthermore, the CSE can be made into suppositories by mixing with a variety of bases such as emulsifying bases or water-soluble bases. The CSE of the present invention can be administered rectally via a suppository. The suppository can include vehicles such as cocoa butter, carbowaxes and polyethylene glycols, which melt at body temperature, yet are solidified at room temperature.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing CSE is placed in proximity to the site of action, so that the local concentration of active agent is increased relative to the rest of the body.

Unit dosage forms for oral or rectal administration such as syrups, elixirs, and suspensions may be provided wherein each dosage unit, for example, teaspoonful, tablespoonful, gel capsule, tablet or suppository, contains a predetermined amount of the compositions of the present invention. Similarly, unit dosage forms for injection or intravenous administration may comprise the compound of the present invention in a composition as a solution in sterile water, normal saline or another pharmaceutically acceptable carrier. The specifications for the novel unit dosage forms of the present invention depend on the particular compound employed and the effect to be achieved, and the pharmacodynamics associated with each active agent in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Nutraceutical formulations: may be defined as "a food or part of a food that offers medical and/or health benefits including prevention or treatment of disease." (Dr. Stephen DeFelice, director of Foundation for Innovation In Medicine). Products range from isolated nutrients, dietary supplements and diets, to genetically engineered designer foods, functional foods, herbal products and processed foods such as cereal, soup and beverages. Functional foods, the most popular term among consumers but far from a product category, are defined by Clare Hasler, Ph.D., of the University of Illinois as foods that include "any modified food or food ingredients that may provide a health benefit beyond the traditional nutrients it contains." Thus, by definition A-CSE, S-CSE and the fractions thereof, in and of themselves constitute nutraceuticals. In addition, A-CSE, S-CSE or the fractions thereof may be added to foods to provide a health benefit.

Nutraceutical formulations of interest include foods for veterinary or human use, including health food bars, drinks and drink supplements, and the like. These foods are enhanced by the inclusion of a biologically active celery seed extract. For example, in the treatment of chronic inflammatory diseases, such as arthritis, the normal diet of a patient may be supplemented by a CSE nutraceutical formulation taken on a regular basis.

Dosages. Depending on the patient and condition being treated and on the administration route, the CSE will generally be administered in dosages of 0.1 mg to 500 mg/kg body weight per day. The range is broad, since in general the efficacy of a therapeutic effect for different mammals varies widely. Similarly the mode of administration can have a large effect on dosage.

A typical dosage may be one tablet taken from two to three times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the formulations are more potent than others. Preferred dosages for a given extract are readily determinable by those of skill in the art by a variety of means. A preferred means is to measure the physiological potency of a given compound.

Amounts ranging between one-tenth and one-half the usual dose of an anti-inflammatory agent, e.g. NSAIDs may be used in the combination formulations provided by the present invention. In this regard, it is expected that amounts of between 2 mg/kg to about 300 mg/kg of NSAIDs will provide therapeutic activity. Of course, the amount/dose used will depend in specific cases on the particular pharmacological characteristics of the NSAID or combination of NSAIDs included.

METHODS OF USE

Formulations of the CSE are administered to a host affected by various chronic or acute conditions, particularly involving pain and/or inflammation. The compounds of the present invention are administered at a dosage that reduces pain or inflammation while minimizing any side-effects. The CSE compounds may also be used to reduce gastric irritation, for example as caused by treatment of an inflammatory condition with NSAIDs.

This invention includes methods for prevention or treatment of acute or chronic inflammation and/or pain comprising administering to a patient in need thereof from about 50 mg/kg/day to about 80 mg/kg/day, preferably from about 30 mg/kg/day to about 50 mg/kg/day, also preferably from about 20 mg/kg/day to about 30 mg/kg/day, also preferably from about 10 mg/kg/day to about 20 mg/kg/day, also preferably from about 5 mg/kg/day to about 10 mg/kg/day, also preferably from about 1 mg/kg/day to about 5 mg/kg/day, of a biologically active celery seed extract of this invention.

This invention includes methods for prevention or reduction of gastric irritation comprising administering to a patient in need thereof from about 50 mg/kg/day to about 80 mg/kg/day, preferably from about 30 mg/kg/day to about 50 mg/kg/day, also preferably from about 20 mg/kg/day to about 30 mg/kg/day, also preferably from about 10 mg/kg/day to about 20 mg/kg/day, also preferably from about 5 mg/kg/day to about 10 mg/kg/day, also preferably from about 1 mg/kg/day to about 5 mg/kg/day, of a biologically active celery seed extract of this invention.

This invention includes methods for both prevention or treatment of inflammation and/or pain and prevention or reduction of gastric irritation comprising administering to a patient in need thereof from about 50 mg/kg/day to about 80 mg/kg/day, preferably from about 30 mg/kg/day to about 50 mg/kg/day, also preferably from about 20 mg/kg/day to about 30 mg/kg/day, also preferably from about 10 mg/kg/day to about 20 mg/kg/day, also preferably from about 5 mg/kg/day to about 10 mg/kg/day, also preferably from about 1 mg/kg/day to about 5 mg/kg/day, of a biologically active celery seed extract of this invention.

Treatment of primates, more particularly humans is of interest, but other animals may also benefit from treatment, particularly domestic animals such as equine, bovine, ovine, feline, canine, murine, lagomorpha, poultry, and the like.

Conditions of interest include musculoskeletal conditions, both inflammatory and non-inflammatory in nature, and acute, subacute or chronic presentation. For example, the composition may be used in the treatment of both the early and late stages of inflammatory arthritis, as well as non-infectious inflammatory arthropathy such as rheumatoid arthritis, bursitis, tendinitis, soft tissue injuries, Sjogren's syndrome, systemic lupus erythematous, psoriatic arthritis, gout and other crystalline arthropathies, capsulitis, carpal tunnel syndrome, myositis, polymyalgia, rheumatica, synovitis and Reiter's syndrome. The compositions of this invention may also be used in the prevention or treatment of erosive osteoarthritis.

Inflammation involves capillary dilation, with accumulation of fluid and migration of phagocytic leukocytes, such as granulocytes and monocytes, to the site of injury or lesion. Inflammation is important in defending a host against a variety of infections, but can also have undesirable consequences in inflammatory disorders. Inflammatory conditions include autoimmune diseases; inflammation caused by bacterial and viral infection, including response to vaccination; local inflammation in response to trauma; graft rejection; graft v. host disease, and the like.

With respect to the prevention or treatment of pain, the compositions of this invention may be orally or topically applied to the patient as an analgesic to prevent or treat acute or chronic pain including muscle pain, lower back pain or sciatica, as well as foot pain such as heel pain, heel spurs, fasciities, metatarsalgia and Achilles tendinitis. The compositions of this invention also have utility in the prevention or treatment of pain associated with osteoarthritis, rheumatoid arthritis and arthritis in general.

Furthermore, the compositions may be administered for dental applications. For example, the compositions of this invention are useful in preventing inflammation after tooth extraction or for treating various forms of gum disease. More specifically, after a periodontist performs gum surgery, an amount of the composition may be taken orally, or in the form of a liquid, gel or cream to be applied directly to the wound, or may be used to bathe the inflamed tissues as a rinse.

Alternatively, in the prevention or treatment of musculoskeletal conditions, the composition may be applied daily in the form of a liquid, cream or gel directly on inflamed tissue. For example, the liquid, cream or gel may be applied generously to the affected area from 1 to 4 times daily and gently massage into the skin until fully absorbed. Following application, an occlusive dressing may be optionally applied for 4 to 10 hours to enhance efficacy. Absorption of the composition can be further enhanced by phoresis, ultrasound and other physical therapy modalities.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

EXAMPLE 1

Fractionation of Ethanolic Extract of Celery Seed to Yield a more Concentrated Biologically Active Extract An ethanol extract of fresh celery seed (A-CSE), harvested and processed in India, (supplied by Beagle International Pty. Ltd., Nerang, Qld. Australia), as a pungent green paste was used as the raw material. This was admixed with an adsorbent for further processing by supercritical fluid extractions (SFE).

Liquid carbon dioxide was contacted with the adsorbed plant material at 30 to 40° C. The pressure employed was programmed to maintain slow incremental increases in pressure to achieve extraction of the compound from the plant material, between about 100 and 300 atmospheres. A pungent amber liquid was obtained representing approximately 15% (w/w) of the original green paste. This material from the supercritical fluid extraction (S-CSE) was further processed to give various subfractions, as follows:

Distillation: 500 mg SFE was fractionated into two (distillate and residue) by distillation at 150° C. and 1.0 mm Hg.

Hydrogenation: 500 mg SFE in 40 ml tetrahydrofuran (THF) was hydrogenated over 20 mg 10% Pd/C at 40 p.s.i. overnight.

Reduction with LiAlH4: 500 mg SFE in 15 ml THF was treated with 100 mg LiAlH4 at 0° C. under argon. After stirring 1 h at room temperature, then adding ethyl acetate and 1.0 M KOH, the product is extracted into dichloromethane.

Double Reduction=Hydrogenation/LiAlH4 Reduction: Hydrogenation was performed as described above, followed by LiAlH4 reduction as above.

Hydrolysis: 500 mg SFE in 20 ml THF was treated with 100 mg LiOH in 20 ml water. Stirring overnight resulted in a clear yellow solution. The products were obtained after evaporation of THF, followed by acidification and extraction.

Hydrolysis/Oxidation: Hydrolysis was performed as above, followed by dissolving product in 10 ml dichloromethane and addition of 100 mg Pd/C. The products were obtained after stirring for 4 h, then dilution with ether and filtration through Celite.

Column Fractionation: 1.00 g SFE was chromatographed on a silica column (150 mm length×30 mm diameter) and eluted with 1–100% diethyl ether in light petroleum.

Fraction 1: that which eluted with 1–20% diethyl ether (37 mg)

Fraction 2: that which eluted with 20–50% diethyl ether (747 mg)

Fraction 3: that which eluted with 100% diethyl ether (152 mg)

Biological activities of these extracts sub-fractions were assessed after oral administration of freshly prepared aqueous dispersions prepared using 0.02% Tween-20 as emulsifier and brief sonication. Reference doses of A-CSE were 150–250 mg/kg; 30–50 mg/kg S-CFE; 10–40 mg/kg various subfractions.

Anti-inflammatory activity was assessed in rats developing adjuvant-induced arthritis after giving test preparations orally (or transdermally) for four days from the time arthritis was first manifest; control animals receiving Tween-20 only. The procedure was exactly that described by M. Whitehouse et al [*Inflammopharmacol* (1997), 5:237–246].

Gastroprotective activity was assessed in fasted (overnight) arthritic rats challenged with 50 mg/kg Ibuprofen given orally to induce gastric bleeding. Test preparations, dispersed with Tween-20, were given orally 20 seconds prior to Ibuprofen. Animals were sacrificed after 2.5 hours to compile a gastric lesion index.

The procedure is further elaborated in K. Rainsford and M. Whitehouse [J. Pharm. Pharmac (1992), 44:476–482].

The extracts and sub-fractions of the celery seed extracts provided in the present invention, summarized in Table 1, showed an anti-inflammatory activity caused no gastric bleeding and are non-volatile, resistant to chemical reduction, but largely destroyed by hydrolysis. These latter properties are not compatible with the chemical structures previously claimed to carry the anti-inflammatory activity.

Moreover in Table 1, it can be seen that column fractionation (S-CSE fraction 1) or LAH reduction of the supercritical fluid extract yield potent anti-inflammatory activity in the absence of butylphthalide and the distillation volatiles from active supercritical fluid which contain butylphthalide, sedanolide and selinene have neither anti-inflammatory or gastroprotective activity. Thus, the claim of butylphthalide and sedanolide being active as anti-inflammatory agents is not supported.

Column fractionation (S-CSE fraction 1 and 3) or double reduction of the supercritical fluid extract demonstrate that the compound(s) responsible for the anti-inflammatory activity can be distinguished from those that provide gastroprotection. The gastroprotective activity identified here has not previously been disclosed.

TABLE 1

Biological Activities and some Chemical Markers of Processed Supercritical Fluid Extracts (SFE)

| Products from: | Anti-inflammatory Activity | Gastro-protective Activity | Markers |
|---|---|---|---|
| S-CSE | ++++ | ++++ | BP. dihydro-BP. tetrahydro-BP. petroselenic acid, methyl ester. |
| Column Fraction 1 | ++++ | + | Absence of BP. Absence of all aromatic compounds. S. Hexadecanoic acid, methyl ester. 9,12-Octadecadienoic acid, methyl ester. 9-Octadecenoic acid. |
| Column Fraction 2 | +/− | +/− | BP. |
| Column Fraction 3 | +++ | +/− | Trace of BP. |
| Distillation Volatiles | − | − | BP, S. Dihydro-BP. |
| Distillation Residues | +++ | +++ | BP. Dihydro-BP. |
| Reduced (LAH) | ++++ | +++ | Absence of S. Absence of BP. Reduced-BP. Octahexanol. 9,12-octadecadien-1-ol. |
| Reduced (Hydrogenated) | ++++ | +++ | BP. Tetrahydro-BP. Hexahydro-BP. |
| Reduced (Double) | ++++ | − | Reduced-BP. Octadecanol. |
| Hydrolysis | + | + | BP. Seco-acid of BP. Hexadecanoic acid. |
| Hydrolysis/ Oxidation | + | + | BP. Seco-acid of BP. |

All products were tested at 10–50 mg/kg.

Markers refer to compounds found in these various fractions. In addition limonene and butylphthalide were-tested at 50 mg/kg and found to possess no anti-inflammatory or gastroprotective activity.

EXAMPLE 2

Treating and Preventing Chronic Pain and Inflammation in Rats Using Biologically Active Celery Seed Extracts An experimental polyarthritis was induced in rats by injecting a mycobacterial arthritogenic adjuvant, Whitehouse et al. (1997) Inflammopharmacology 5:237–246 The animals were then treated for 4 days only (days 10–13 after initiation of inflammation). Paw thickness was measured using a micrometer screw gauge on day 14.

The data in Table 2 demonstrate that S-CSE is approximately 7 fold more active than the starting material A-CSE and that S-CSE has a specific activity equivalent to, and in some cases greater than aspirin and NSAIDs such as ibuprofen and naproxen. Moreover, the data suggest that not all sources of celery seed are equivalent, nor all methods of supercritical fractionation, as regards the production of biologically active material.

TABLE 2

Efficacy of Celery Seed in Treating Experimental Polyarthritis in Rats

| | | Mean % Inhibition of Swelling/Arthritis Score | | | |
|---|---|---|---|---|---|
| Treatment (per os) | Dose mg/kg per day | Rear Paw Swelling | Fore Paw Swelling | Arthritis Score[3] | No. Rats per group |
| A-CSE (Beagle) | 350 | 80 | 82 | 93 | 12 |

TABLE 2-continued

Efficacy of Celery Seed in Treating Experimental Polyarthritis in Rats

| Treatment (per os) | Dose mg/kg per day | Rear Paw Swelling | Fore Paw Swelling | Arthritis Score[3] | No. Rats per group |
|---|---|---|---|---|---|
| S-CSE (Beagle) | 50 | 85 | 91 | 60 | 9 |
| S-CSE (Chinese Celery Seed)[1] | 50 | 29 | 12 | 20 | 4 |
| S-CSE (Commercial)[2] | 50 | (−15) | 17 | 0 | 4 |
| Aspirin | 150 × 2 | 40 | 24 | 25 | 5 |
| Ibuprofen | 50 | 38 | 39 | 36 | 5 |
| Naproxen | 25 | 57 | 36 | 64 | 5 |

Animals dosed for 4 days only (days 10–13 after initiation of inflammation). Measurements made on day 14.
[1]Prepared by Craig Davis from Chinese instead of Indian Celery Seed
[2]Commercial $CO_2$ extract of celery seed, origin of seed not identified, made by Finzelberg, Andernach, Germany
Arthritis score was assessed by an independent observer
The residue from supercritical fractionation was tested at 300 mg/kg and found to have little or no anti-inflammatory activity.

The data in Table 3 indicate that S-CSE and certain of its subfractions are effective in preventing, as well as treating adjuvant arthritis in rats. In addition, known components of celery seed, such as limonene, bergapten, butylphthalide and petroselenic acid methyl ester are without such activity. Furthermore, this ability to ablate inflammation is not shared by conventional anti-inflammatory agents (like ibuprofen, naproxen or aspirin) or commercial celery seed oils or supercritical extracts. However, drugs with disease-modifying activity, such as lobenzarit and cyclosporine, which are known to be immunomodulators are capable of ablating the onset of arthritis in this model (Haynes D R et al. Inflamm Res 45:159–165, 1996) and have been used in the treatment of arthritis.

TABLE 3

Arthritis-ablating activity of some CSE components

| Additive (5 mg/rat) | Mean Arthritis Score (AS) | No rats |
|---|---|---|
| None | 3.1+ | 10 |
| S-CSE | 1.3+ | 7 |
| S-CSE-H₂ reduction | 0.6+ | 6 |
| S-CSE-LAH reduction | 0.2+ | 6 |
| S-CSE-Hydrolysed | 1.3+ | 3 |
| S-CSE-Distillate | 3.4+ | 6 |
| S-CSE-Distill. residue | 0.5+ | 6 |
| S-CSE | 0.8+ | 3 |
| S-CSE (Commercial)[1] | 3+ | 3 |
| Celery seed oil[2] | 2+ | 3 |
| Limonene | 3+ | 6 |
| Petroselenic acid methyl ester | 2.3+ | 3 |
| Butylphthalide | 2+ | 3 |
| Bergapten | 2.7+ | 3 |

[1] Commercial $CO_2$ extract of celery seed, origin of seed not identified, made by Finzelberg, Andernach, Germany
[2] Commercial celery seed oil made by Bronsen & Jacob Protocol: test materials incorporated into an arthritigenic adjuvant (0.5 mg *Mycobacterium. tuberculosis* in 0.1 ml in jojoba bean oil) for injection into tailbase of female Dark Agouti rats. Arthritis scored 15 days later on scale 0–5+ by independent assessor.

Drugs which had no effect (AS 2.5+) include 18 NSAIDs, dapsone, azathioprine, chlorambucil and all commercial celery seed oils tested (n=12). Most of these (drugs and oils) were tested at 10 mg/rat.

EXAMPLE 3

Treating and Preventing Acute Pain and Inflammation in Rats Using Biologically Active Celery Seed Extracts The pain model used was that based on the standard model of Randell & Selitto in which rat paws were pre-swollen with a carageenan injection and then pressure sensitivity assessed with or without a dose of celery extract (Randall L O, Sellito J J Arch Int Pharmacodyn Ther 1957:111:409–419).

Nurofen (OTC ibuprofen) at 200 mg/kg completely abolished the pain as determined by lack of vocalisation when a standard pressure was applied to rat paws swollen by pre-injected carrageenan (0.6 mg/paw). This analgesia lasted at least 3.5 hours. The celery extract (A-CSE) gave the same response at 500 mg/kg but there was no attempt to define a dose-response. The concentrate produced by super critical fractionation, S-CSE, was equipotent at 70 mg/kg, and therefore on a weight basis was superior to Nurofen. These data indicate that the original extract (A-CSE) can relieve acute pain, but that S-CSE is more active, i.e. has a 7 fold higher specific activity.

EXAMPLE 4

Treating and Preventing Pain and Inflammation Using Biologically Active Celery Seed Extracts in Combination with Drugs and Herbals to Provide Additive or Synergistic Effects Chronic Inflammation To evaluate therapeutic efficacy against a chronic (established) inflammation, polyarthritis was initiated in female Dark Agouti or Wistar rats on "Day O" by injecting 800 μg heat-killed Mycobacterium tuberculosis in 100 μl squalane (constituting a 'complete' Freund's adjuvant) into the tail base. The test drugs/formulations were given on and after Day 10 to treat the established arthritis. The polyarthritis is usually manifest from Day 12 as local inflammation and ulceration in the tail, inflammation in all paws and inflammatory lesions on forepaws and ears.

Inflammation was evaluated using a micrometer to measure changes in rear paw and tail thickness, and by visual estimates of the severity of front paw swelling and inflammation. Animals were sacrificed by cervical dislocation on or before Day 18 and checked for gastric lesions and other non-articular pathologic changes. Statistical significance was evaluated by using the standard Student 't test' described in "Statistical Methods", 8th edition, G W Snedecor, W G Cochran, Iowa State University Press, Ames, Iowa (1989).

To evaluate early i.e. rapid-acting therapeutic efficacy, carrageenan (1 mg in 0.1 ml saline) was injected into rear paws of rats to elicit a rapid onset (acute) inflammation. The ensuing paw edema was measured by the increase in paw thickness with a micrometer over the subsequent three hour period at hourly intervals.

The test drug formulations were given orally 45 minutes before injecting the carrageenan.

A striking synergistic effect was found when Ibuprofen was administered to rats with chronic inflammation developing an experimental polyarthritis in all 4 paws and also affecting the tail joints. In groups of eight animals, Ibuprofen given for four successive doses orally at 30 mg/kg only suppressed arthritic paw swelling by 38 percent. Low doses of A-CSE (50 mg/kg) or S-CSE (5 mg/kg) inhibited polyarthritis by 30 percent and 35 percent respectively demonstrating that celery extracts had significant anti-inflammatory activity in this model of chronic inflammation.

Super critical fractionation of A-CSE to yield S-CSE in this instance increased specific activity 10 fold. Combining this dose of the Ibuprofen with either A-CSE or S-CSE yielded inhibition of the arthritic inflammation that was consistently greater than 90 percent (n=10 rats/group). This latter remarkable finding establishes that using a combination of celery extract with the gastro-toxic NSAID to reduce/abolish gastro-toxicity does not interfere with the anti-arthritic action of either the NSAID or the celery extract; but actually reinforces the potency of the individual components.

Acute Inflammation

In the commonly employed test for evaluating rapid-acting NSAIDs based on suppressing the carrageenan-induced paw edema, it was found that the effective dose for 50 percent reduction of the paw edema ($ED_{50}$) was 200 mg/kg for aspirin, 45 mg/kg for Ibuprofen and 6 mg/kg for Ketoprofen. The corresponding $ED_{50}$ values for biologically active celery seed extract preparations used alone (without an NSAID) were greater than 500 mg/kg for A-CSE or 100 mg/kg for S-CSE.

Lower doses of Ibuprofen (15 mg/kg) and Ketoprofen (1 mg/kg) gave only 19 and 12 percent inhibition of paw swelling respectively, not statistically significant for the small number of animals (n=6). However when either the Ibuprofen or Ketoprofen was co-administered with S-CSE (50 mg/kg) in these same experiments, the inhibition of paw swelling was significantly amplified to 61 and 46 percent respectively.

Other experiments indicated that the antipyretic effects of ibuprofen (50 mg/kg), ketoprofen (10 mg/kg), or aspirin (150 mg/kg) in rats with an experimental fever (induced by prior inoculation of 1 gm/kg brewer's yeast nine hours previously) were not reduced by co-administering celery extracts at gastro-protectant levels.

EXAMPLE 5

Treating and Preventing Gastrointestinal Irritation Using Biologically Active Celery Seed Extracts To evaluate gastric injury caused by aspirin/NSAIDs, administered alone or in combinations with celery seed extract, these drugs were given (orally or parenterally) to rats which had been pre-sensitised by disease stress (induced five days previously either by injecting an arthritigenic adjuvant or 0.1 ml oleyl alcohol into the tail base to incite severe local inflammation). Rats were permitted free access to water but routinely fasted for 16 hours prior to dosing them for the gastrotoxicity assay, to facilitate inspection of the gastric lining post mortem. The animals were-sacrificed 2.5 hours after administering the aspirin/NSAID.

Ibuprofen given to pre-inflamed female Wistar rats as either the free acid (obtained from Sigma Chemical Co. USA) or as a proprietary formulation for over-the-counter use (Nurofen, Boots-Knoll) regularly causes gastric bleeding with the mean number of haemorrhagic lesions (+/−SD) being 42+/−06 (n=90 rats) for a standard dose of 50 mg/kg administered as a suspension in a volume of 5 ml/kg.

Co-administration of the celery extract in doses of 150 mg/kg of A-CSE or 20 mg/kg of S-CSE administered in a volume of 10 ml/kg, consistently reduced by 70 percent the mean number of gastric lesions elicited by the Ibuprofen at this probing dose (50 mg/kg). Furthermore, the severity as well as the total number of lesions was significantly reduced from a mean grade of 3.4+ to 1.9+ (on a scale of 0 to 4+) by the co-administration of the celery extract. More strikingly, the number of animals which had no macroscopically detectable gastric bleeding was increased from 7 percent (Ibuprofen with no celery, n=90 rats) to 29 percent with celery extracts (n=67 rats). The efficacy of the celery supplement was attested by these three criteria, namely reduction in number of lesions, reduction in severity of lesions, and total absence of lesions in a significant proportion of the celery-dosed rats.

In parallel studies aspirin (100 mg/kg), Naproxen (10 mg/kg) and Ketoprofen (5 mg/kg) given orally and Piroxicam (5 mg/kg) given intraperitoneally to pre-inflamed rats, also caused significant gastric lesions and bleeding (90 percent incidence); the severity of which was likewise reduced by 70 percent with these same doses of A-CSE or S-CSE. In earlier studies A-CSE (500 mg/kg) also was shown to reduce the extent of gastric lesions induced by alcohol in rats.

In further studies testing for the specificity of the celery extract in conferring gastro-protection, it was found that co-administration of various 'packing' materials in place of the celery (e.g. milk, ground bran, ground carrot, ground rat feces, mashed banana, etc.), at doses of 300 mg/kg or more, failed to provide significant gastro-protection, i.e. reduction in the mean number of Ibuprofen- or Naproxen- or Ketoprofen-induced gastric lesions never exceeded 25 percent. In yet other studies it was found that the optimal effect of the gastroprotective celery extract was obtained when it was given concurrently with the NSAID, preferably in a specifically formulated admixture.

EXAMPLE 6

Evidence that Gastroprotective Activity of Celery Seed Extract is Not Associated with the Major Flavanoids Present in Celery Seed Three unidentified fractions have been isolated from A-CSE by means of a 5 ml pre-packed quaternary amine solid phase mini-column (Waters). The column was eluted sequentially with acidified water (adjusted to pH 3 with dilute HCl), methanol/water (10:90), petroleum ether (60–80 BPt), methanol and ethyl acetate. These three components (coded A, B, and C) were identified by TLC on GF-254 silica gel plates in methanol/water (90:10) as having Rf values of 0.70, 0.38 and 0.20.

These fractions did not correspond to 3 commonly observed flavanoids present in CSE, quercitin, myricetin and limonene, which have had Rf values of 0.89, 0.62 and 0.86 in this system. There were a total of 10 components were present in the A-CSE starting material but only 3 were eluted from the column and quercetin, myricetin and limonene (determined by TLC with pure standards of these compounds) were not amongst those that were eluted.

All three components, A, B, C, at concentrations equivalent to that from 30 µg/mL of the original A-CSE caused stimulation of production of prostaglandin E2 when incubated with pig gastric (fundic) mucosal explants when the assay was performed as described in Rainsford et al., 1995, Inflammopharmacology 3:299–310. Component B showed the greatest stimulatory effect having 10 times the stimulation over control, while the other two components had 4 times the stimulatory effect on PGE-2 production compared with control. Stimulation of prostaglandin E2 production is one mechanism whereby ulcer healing occurs.

Under the same conditions and in contrast, pure samples of quercetin and myricetin, but not limonene, (all obtained from Aldrich Chemical Co.), at a concentration of 10 µmol/L, inhibited production of prostaglandin E2. These results demonstrate that celery seed extract (A-CSE) contains both prostaglandin inhibitory and stimulatory components. The prostaglandin E2 stimulatory compounds can be separated by column chromatography. These 3 as yet unidentified components may contribute to the anti-ulcer effects of CSE against NSAID induced gastric injury and also may foster ulcer healing.

EXAMPLE 7

Treating and Preventing Pain, Inflammation and Gastrointestinal Irritation in Pets and Farm Animals Alone or by Incorporation in Foods or Food Supplements The tablet form of the alcoholic celery seed extract has been used extensively in horses and dogs to provide analgesia in mild, chronic pain. The typical dose for horses is three tablets a day and one tablet a day for dogs. The extract as described in EXAMPLE 1, S-CSE and some of S-CSE subfractions due to their greater specific activity and greatly reduced amounts of flavoring components, which can be unpalatable or bitter in large doses, would be particularly suitable for incorporation into animal feed.

What is claimed is:

1. A method for the treatment of acute or chronic inflammation, the method comprising:
   administering an effective dose of a biologically active celery seed extract produced by supercritical fluid extraction of an ethanolic extract of fresh celery seed.

2. The method of claim 1, further comprising administering a second anti-inflammatory drug.

3. The method of claim 2, wherein said second anti-inflammatory drug is an NSAID.

4. The method of claim 3, wherein said NSAID is selected from the group consisting of fenoprofen calcium, nalfon, flurbiprofen, Ansaid, ibuprofen, ketoprofen, naproxen, anaprox, aflaxen, oxaprozin, diclofenac sodium, diclofenac potassium, cataflam, etodolac, indomethacin, ketorolac, nabumetone, sulindac, tolmetin sodium, fenamates, meclofenamate sodium, mefenamic acid, piroxicam, salicylic acid, diflunisal, aspirin, oxyphenbutazone, and phenylbutazone.

5. The method of claim 4, wherein said supercritical fluid extraction is performed at temperatures ranging from 30 to 40° C., between about 100 and 300 atmospheres, using carbon dioxide admixed with methanol.

6. A method for treatment of acute or chronic inflammation comprising administering to a patient in need thereof, from about 20 mg/kg/day to about 50 mg/kg/day of a biologically active celery seed extract produced by supercritical fluid extraction of an ethanolic extract of fresh celery seed.

7. A method for treatment of acute or chronic inflammation comprising administering to a patient in need thereof, from about 10 mg/kg/day to about 20 mg/kg/day of a biologically active celery seed extract produced by supercritical fluid extraction of an ethanolic extract of fresh celery seed.

8. A method for treatment of acute or chronic inflammation comprising administering to a patient in need thereof, from about 1 mg/kg/day to about 10 mg/kg/day of a biologically active celery seed extract produced by supercritical fluid extraction of an ethanolic extract of fresh celery seed.

* * * * *